United States Patent [19]

Chamberlin, Sr.

[11] Patent Number: Plant 6,991

[45] Date of Patent: Aug. 22, 1989

[54] PLUM TREE, "DEL REY SUN"

[75] Inventor: Thomas O. Chamberlin, Sr., Visalia, Calif.

[73] Assignees: Metzler Investments; Metropolitan Life Insurance Company, both of Del Rey, Calif.

[21] Appl. No.: 234,890

[22] Filed: Aug. 22, 1988

[51] Int. Cl.[4] ..... A01H 5/00

[52] U.S. Cl. ..... Plt./38

[58] Field of Search ..... Plt. 38

*Primary Examiner*—Robert E. Bagwill

*Attorney, Agent, or Firm*—Worrel & Worrel

[57] ABSTRACT

A new and distinct variety of plum tree which is characterized by a date of maturity for harvesting and shipment of approximately June 15 through June 20 under the ecological conditions prevailing at Del Rey, Calif., the subject variety further distinguished as to novelty by producing a black plum which has a tough skin, a firm yellow colored flesh and exceptional storage and shipping characteristics.

1 Drawing Sheet

BACKGROUND OF THE NEW VARIETY

The present invention relates to a plum tree denominated varietally as "Del Rey Sun" and more particularly to such a plum tree which produces freestone fruit having a larger size and an attractive black skin color and which further is characterized principally as to novelty by producing fruit which are ripe for commercial harvesting and shipment approximately June 15 through June 20 in the central portion of the San Joaquin Valley of central Calif.

The applicant has devoted a substantial portion of his professional career and adult life to the development of new commercial varieties of fruit trees. In this regard, the applicant, as a matter of course, has routinely collect mixed lots of seeds from the assorted ranches under his direction and control and has thereafter germinated and evaluated the trees produced therefrom in an effort to determine whether any new varieties of fruit trees are present. The present variety of plum tree "Del Rey Sun" resulted from the aforementioned procedures.

ORIGIN AND ASEXUAL REPRODUCTION OF THE NEW VARIETY

The new and distinct variety of plum tree hereof was a chance seedling derived from a mixed lot of seed procured from Ranch No. 5 of the H. P. Metzler & Sons Company located at 5286 South Del Rey Ave., Del Rey, Calif. in 1979. This mixed lot of seed was planted in the Winter of 1979 and 1980 and the plants resulting therefrom were later observed. The first fruit were produced in 1982. The new variety produced an attractive black plum within a size range and harvesting period which were noted at the time of observation to be quite promising. In an effort to confirm these characteristics, the applicant, in 1983, collected bud wood from the parent tree and thereafter budded this same plant material into trees which are located in the test block on Ranch #20, at the same address in Del Rey, Calif. The budded test trees have continually been observed by the applicant and it has subsequently been determined that the progeny produced from these test trees have the same identical characteristics as the parent tree.

SUMMARY OF THE NEW VARIETY

The "Del Rey Sun" variety of plum tree hereof is characterized principally as to novelty by bearing fruit which have a black skin color and which are ripe for commercial harvesting approximately June 15 through June 20, approximately midway between the harvesting dates for the Black Beaut Plum Tree (U.S. Plant Pat. No. 3,617) and the Santa Rosa Plum Tree (unpatented), these particular plum varieties maturing in approximately the same season, and which further is characterized as to novelty by being freestone by nature and having a tough skin which imparts noteworthy shipping and handling characteristics to the variety.

BRIEF DESCRIPTION OF THE DRAWINGS

The accompanying drawing is a color photograph of five mature fruit, one of which has been divided in the axial plane to show the flesh and pit characteristics, together with a twig bearing representative leaves which displays the coloration of the top and bottom surfaces thereof, all of the subject variety.

DETAILED DESCRIPTION

Referring more specifically to the pomological details of this new and distinct variety of plum tree, the following has been observed under the ecological conditions prevailing at the applicant's employer's orchard which is located at 5286 South Del Rey Ave. in Del Rey, Calif. All major color shape plate identifications are by reference to the Inter-Society Color Council, National Bureau of Standards. However, common color names are also employed occasionally.

TREE

Size: Average:

Vigor: Vigorous:

Figure: Average, with upright growth, depending upon pruning practices.

Productivity: Good. It has been determined that the variety "Del Rey Sun" probably is self-pollinating, however, the variety appears to produce a better crop when it is planted in the immediate vicinity of other plum varieties which have approximately the same blossoming date.

Regularity of bearing: Regular, providing the new variety is planted in the vicinity of other plum varieties which have approximately the same blossoming date.

Trunk:

*Diameter.*—Average.

*Surface texture.*—Noteworthy, the subject variety has characteristically long cracks in the bark which may perhaps act as lenticels.

*Lenticels.*—The variety has approximately six to eight average sized lenticels per square inch.

*Surface texture.*—Color — Brown, (62. d. gy. Br.).

*Lenticels.*—Color — Light brown, (76. l. y Br.).

*Cracks.*—Dimensions — The cracks are approximately six to eight inches in length (152.4 mm–203.2 mm.), and are approximately $\frac{1}{8}''$ in width, (3.175 mm). Color — The cracks appear to be a lighter color than that of the surrounding bark.

Branches:

*Size.*—Average.

*Surface texture.*—Color — The color of the branches appears to be similar to that of the trunk, brown, (62. d. gy. Br.).

*Lenticels.*—The lenticels are approximately the same dimensions and color as that displayed on the trunk.

LEAVES

Size:

*Generally.*—Average.

*Length.*—Variable, approximately $3\frac{1}{2}''$ to $3\frac{3}{4}''$, (88.9 mm. to 95.2 mm).

*Width.*—Variable, approximately $1\frac{1}{2}''$ to $1\frac{3}{4}''$, (38.1 mm. to 44.4 mm).

Shape: Lanceolate.

Color:

*Upper surface.*—Green, (126. d. Ol G).

*Lower surface.*—Pale green, (125. m. Ol G).

Marginal form: Doubly serrate.

Glands: None evident.

Stipules: One pair of stipules normally will be located at the base of the leaf.

Petiole:

*Length.*—Approximately $\frac{5}{8}''$ (15.87 mm.).

*Thickness.*—Approximately 1/16", (1.58 mm.).

Stem glands: Not evident.

Stipules: One pair of stipules usually are located at the base of the petiole, and are approximately $\frac{1}{4}''$ in length (6.35 mm.).

Flower buds:

*Size.*—The flower buds, just prior to opening, have a diametral dimension of approximately 3/16" (4.76 mm.).

*Form.*—Generally — Nearly round.

*Petiole.*—Length — Approximately $\frac{1}{4}''$ (6.35 mm.) just prior to flowering.

*Bud set.*—Position — The bud set occurs, as a general matter on the spurs. Each spur sets a multiplicity of buds, however, each bud appears to develop by itself.

*Color.*—Just prior to opening the flower buds are a dull green, (120 m.Y G.)

Flowers:

*Date of bloom.*—Approximately February 25 to March 1 at Del Rey, Calif.

Size:

*Petals.*—Each petal is roundish in appearance and has a diametral dimension of approximately $\frac{1}{4}''$, (6.35 mm.). Color — White (263. white). Flowering Characteristics — The subject variety produces one flower per bud. Petiole — Length — Approximately 5/16" (7.93 mm.) at full bloom.

FRUIT

Maturity when described: Ripe for commercial harvesting and shipment approximately June 15 through June 20 at Del Rey, Calif.

Uniformity: Good.

Diameter in the suture plane: Approximately $2\frac{1}{8}''$ to $2\frac{1}{2}''$ (approximately 53.9 mm. to 63.5 mm.).

Diameter transverse in the suture plane: Approximately $1\frac{3}{4}''$ to 2", (44.4 mm. to 50.8 mm).

Diameter transverse at right angles to the suture plane: Approximately $2\frac{1}{8}''$ to $2\frac{3}{8}''$, (53.9 mm. to 60.3 mm.).

Form:

*Uniformity.*—Good.

*Shape.*—Generally roundish, however the variety typically displays a flat apex area.

*Suture.*—Generally — Very smooth and appears slightly receded.

*Ventral surface.*—Generally — Slightly flat.

*Pistil point.*—Smooth.

*Base.*—Shape — Slightly rounded.

*Apex.*—Shape — Slightly rounded and may occasionally appear flat.

Stem:

*Length.*—Approximately $\frac{1}{2}''$, (12.7 mm.).

*Diameter.*—Approximately 1/16", (1.58 mm).

*Stem cavity.*—Shape — Round. Depth — Variable, approximately $\frac{1}{4}''$ to 5/16" (6.35 mm.–7.93 mm.).

Skin:

*Thickness.*—Similar to other plum varieties, approximately 1/64", (0.397 mm.).

*Texture.*—Very smooth, however the skin is quite strong and tough.

*Tendency to crack.*—Not observed.

*Color.*—Black (267. Black).

Flesh:

*Color.*—Yellow (86. l. Y.).

*Texture of pit cavity.*—Generally — Smooth.

*Color of pit cavity.*—Dark Yellow, (88. d. Y.).

*Juice production.*—Very juicy.

*Flavor.*—Good, smooth, and not very tart.

*Aroma.*—Slight.

*Fibers.*—Not evident.

*Texture.*—Smooth and crisp.

*Ripening.*—Even.

*Eating quality.*—Very good.

Stone:

*Generally.*—Freestone when ripe.

*Fibers.*—None evident.

*Size.*—Length — Approximately $\frac{5}{8}''$, (15.87 mm.). Width — Approximately 9/16", (14.28 mm.). Thickness — Approximately 5/16", (7.93 mm.).

*Form.*—Nearly round and somewhat slightly flat.

*Color.*—A dull yellow (72. d. OY).

*Base.*—Generally — Very small and slightly flat.

*Sides.*—Texture — Nearly smooth.

*Ridges.*—Not present.

Use: Fresh market.

Storage quality: Noteworthy. The subject variety has been held in cold storage in excess of Thirty (30) days with no deleterious effects noted.

Shipping quality: The subject variety has not been shipped in bulk, however the tough skin and the firm texture of the flesh at harvesting time indicates that the subject variety will have noteworthy shipping and handling characteristics.

Although the new variety of plum tree possesses the described characteristics as a result of the growing conditions prevailing in Del Rey, Calif., in the central part of the San Joaquin Valley, it is to be understood that various of the usual magnitude and characteristics incident to changes in growing conditions, fertilization, pruning and pest control are to be expected.

Having thus described my new variety of plum tree, what is new and desired to be secured by Letters Patent is:

1. A new and distinct variety of plum tree substantially as illustrated and described and which is characterized principally as to novelty by bearing fruit which are uniformly shaped and have an attractive black skin color and which further ripen for harvesting and shipment approximately June 15 through June 20 in the San Joaquin Valley of Central Calif., the subject variety maturing in that period of the season approximately midway between the Black Beaut Plum (U.S. Plant Pat. No. 3,617) and the earliest harvesting date of the Santa Rosa Plum Tree (unpatented) at Del Rey, Calif., and which further has a tough skin and a firm yellow flesh, the fruit of the new variety of plum tree having an excellent flavor and exceptional handling and shipping characteristics.

* * * * *

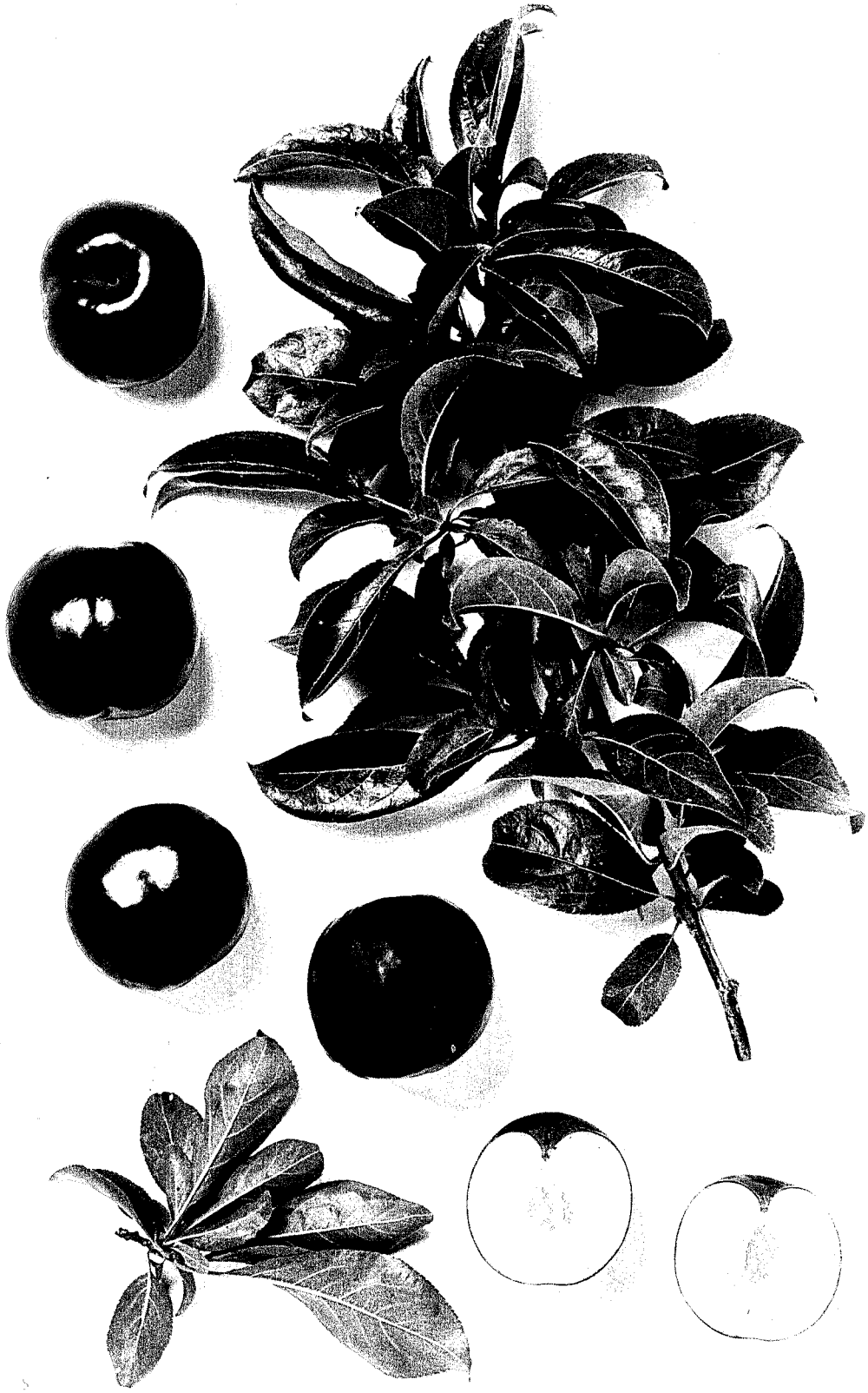

UNITED STATES PATENT AND TRADEMARK OFFICE

CERTIFICATE OF CORRECTION

PATENT NO. : PP 6,991

DATED : August 22, 1989

INVENTOR(S) : Thomas O. Chamberlin, Sr.

It is certified that error appears in the above-identified patent and that said Letters Patent is hereby corrected as shown below:

Column 5, Line 5

Delete "various" and
Insert ---variations---

Signed and Sealed this

Third Day of July, 1990

*Attest:*

*Attesting Officer*

HARRY F. MANBECK, JR.

*Commissioner of Patents and Trademarks*